(12) United States Patent
Limousin et al.

(10) Patent No.: US 7,630,770 B2
(45) Date of Patent: Dec. 8, 2009

(54) MANAGEMENT OF RESPIRATORY PAUSES OF HYPOPNEA IN AN ACTIVE IMPLANTABLE MEDICAL DEVICE OF THE CARDIAC PACEMAKER, DEFIBRILLATOR, CARDIOVERTOR OR MULTISITE DEVICE TYPE

(75) Inventors: Marcel Limousin, Paris (FR); Guido Gaggini, Milano (IT)

(73) Assignee: ELA Medical S.A.S., Montrouge (FR)

( * ) Notice: Subject to any disclaimer, the term of this patent is extended or adjusted under 35 U.S.C. 154(b) by 960 days.

(21) Appl. No.: 10/693,833

(22) Filed: Oct. 24, 2003

(65) Prior Publication Data
US 2004/0138718 A1 Jul. 15, 2004

(30) Foreign Application Priority Data
Oct. 25, 2002 (FR) .................................. 02 13356

(51) Int. Cl.
*A61N 1/365* (2006.01)
(52) U.S. Cl. ........................................................ 607/42
(58) Field of Classification Search .............. 607/17–20, 607/23–24, 42
See application file for complete search history.

(56) References Cited

U.S. PATENT DOCUMENTS

| 5,304,208 | A | 4/1994 | Inguaggiato et al. ........... 607/17 |
| 5,454,838 | A | 10/1995 | Vallana et al. ................. 607/19 |
| 5,496,351 | A | 3/1996 | Plicchi et al. .................. 607/17 |
| 5,722,996 | A | 3/1998 | Bonnet et al. .................. 607/17 |
| 5,766,228 | A | 6/1998 | Bonnet et al. .................. 607/16 |
| 5,974,340 | A | 10/1999 | Kadhiresan ................... 607/18 |
| 6,126,611 | A * | 10/2000 | Bourgeois et al. ............ 600/529 |
| 6,141,590 | A | 10/2000 | Renirie et al. ................. 607/20 |
| 6,161,042 | A * | 12/2000 | Hartley et al. ................. 607/20 |
| 6,253,106 | B1 | 6/2001 | Legay et al. .................... 607/9 |
| 6,415,183 | B1 * | 7/2002 | Scheiner et al. ............... 607/42 |
| 6,459,929 | B1 * | 10/2002 | Hopper et al. ............... 600/513 |
| 6,574,507 | B1 | 6/2003 | Bonnet ........................ 607/20 |
| 6,604,002 | B2 | 8/2003 | Molin ......................... 607/28 |
| 2001/0034540 | A1 | 10/2001 | Molin ......................... 607/20 |
| 2003/0163059 | A1 | 8/2003 | Poezevera et al. ............. 600/34 |
| 2003/0195571 | A1 * | 10/2003 | Burnes et al. .................. 607/9 |

FOREIGN PATENT DOCUMENTS

| EP | 0 940 155 A2 | 9/1999 |
| EP | 1 151 718 A2 | 11/2001 |

* cited by examiner

*Primary Examiner*—George R Evanisko
*Assistant Examiner*—Alyssa M Alter
(74) *Attorney, Agent, or Firm*—Orrick Herrington & Sutcliffe, LLP

(57) ABSTRACT

Improved management of respiratory pauses (apnea) or hypopnea in an active implantable medical device of the cardiac pacemaker, cardiovertor and defibrillator types including multisite devices. This device operates to analyze the patient's respiratory activity, detect the occurrence of respiratory pauses (apnea) or diminutions (hypopnea), analyze the contractility of the myocardium, for example, by measurement of the intracardiac impedance or the endocardial acceleration, and detect the occurrence of a variation of the hemodynamic state. In the event of a significant variation of the hemodynamic state (i.e., contractility) detected in relation to the detection of an apnea or of an hypopnea, the device modifies conditionally and temporarily an operating parameter of the device, for example, the frequency of stimulation, the atrio-ventricular delay or to trigger a multistate stimulation to compensate.

13 Claims, 2 Drawing Sheets

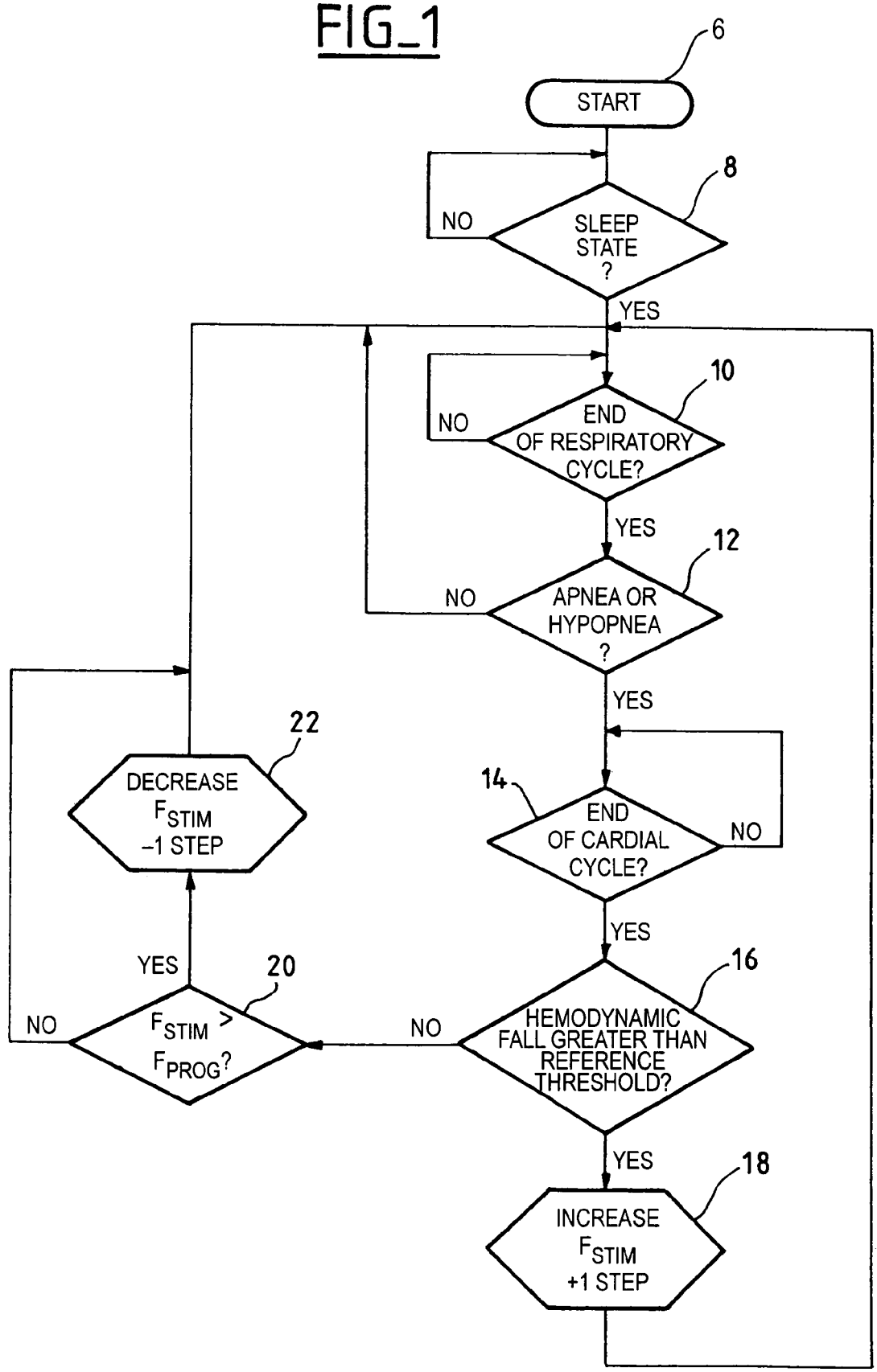
FIG_1

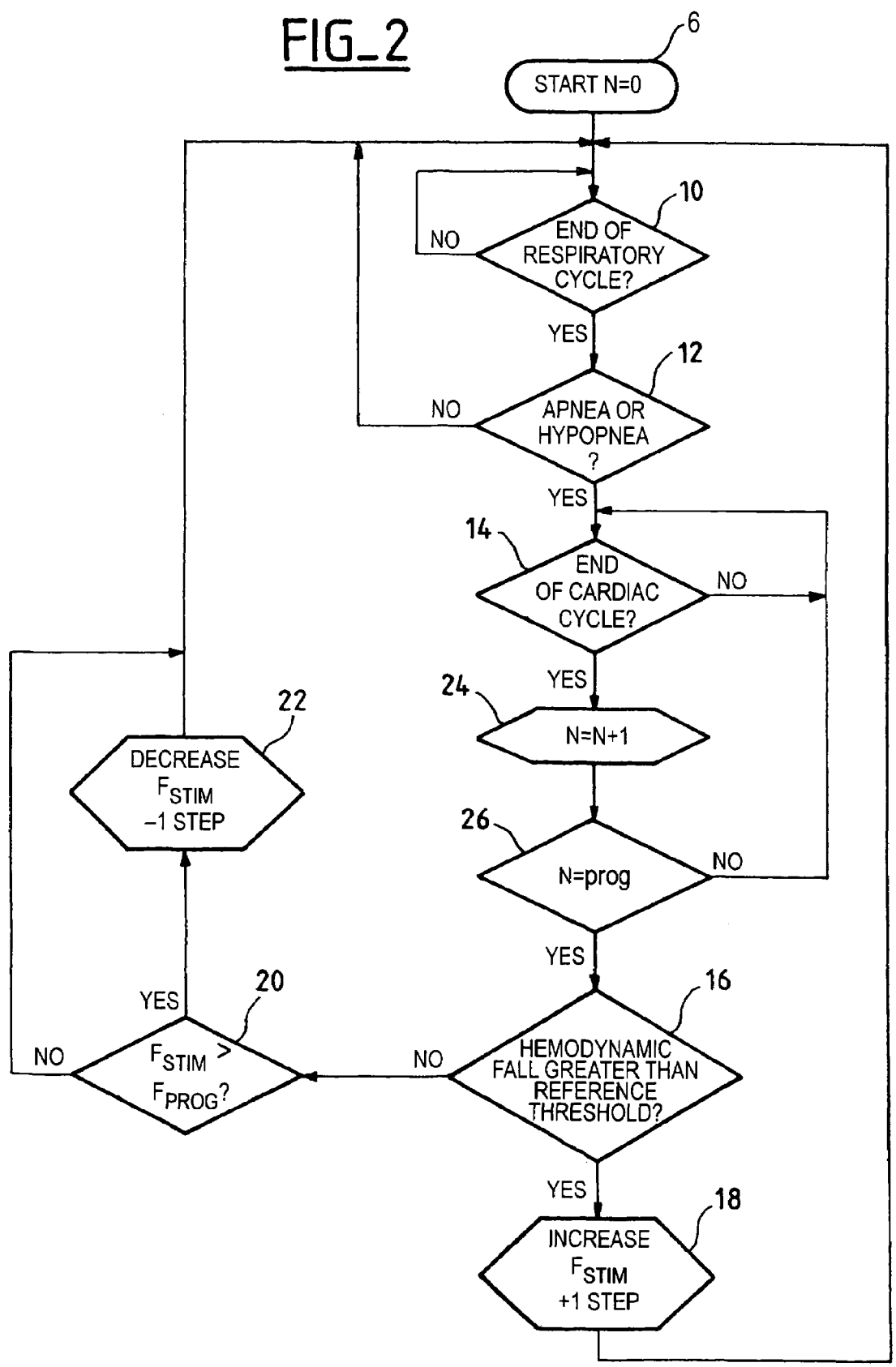

MANAGEMENT OF RESPIRATORY PAUSES OF HYPOPNEA IN AN ACTIVE IMPLANTABLE MEDICAL DEVICE OF THE CARDIAC PACEMAKER, DEFIBRILLATOR, CARDIOVERTOR OR MULTISITE DEVICE TYPE

FIELD OF INVENTION

The present invention relates to "active implantable medical devices" as such devices are defined by the Jun. 20, 1990 directive 90/385/CEE of the Council of the European Communities, and more particularly to cardiac pacemaker, defibrillator and/or cardiovertor devices, including multisite cardiac stimulation devices, that are able to deliver to the heart stimulation pulses of low energy for the treatment of cardiac rhythm disorders.

BACKGROUND OF THE INVENTION

It is known from, for example, in the EP-A-0 970 713 and its corresponding U.S. Pat. No. 6,574,507 B1, commonly assigned herewith to ELA Medical S.A. Montrouge, France, to diagnose and treat respiratory disorders such as the apnea revealing a pathology known as "sleep apnea syndrome" (SAS). In a general manner, this SAS respiratory pathology is characterized by the frequent occurrence of apnea during a phase of sleep of the patient (e.g., at least 10 to 20 events per hour). An "apnea" (also known as a respiratory pause) is defined as a temporary cessation (or stop) of the respiratory function of a duration that is greater than approximately 10 seconds. The SAS pathology also can be characterized by the occurrence of hypopnea under the same frequency conditions. A "hypopnea" is defined as a significant decrease (but without interruption) of the respiratory flow, typically a decrease of more than 50% as compared to a previously acquired respiratory flow reference.

The interruption or the reduction of the respiratory flow involves a reduction in the oxygen concentration of blood (also known as the oxygen saturation), and the occurrence of unconscious, micro waking-up events. This pathology, which is found in more than 50% of those patients patients suffering from a cardiac insufficiency condition, has as a consequence inter alia a diurnal somnolence, a loss of attention, an increase in the risks of road (automobile) accidents, and a higher incidence of hypertension.

The above mentioned EP-A-0 970 713 and U.S. Pat. No. 6,574,507 B1 discloses apparatus and methods for diagnosing the occurrence of an apnea from a minute-ventilation signal ("signal VE," also designated as "signal Mv"), which is a parameter of physiological preponderance generally obtained by a measurement of intrathoracic impedance. The signal MV provides a continuous indication of the respiration rate and the respiratory flow volume of the patient. If an apnea occurs during a phase (also called a "state") of sleep of the patient (the sleep state of the patient can be, for example, indicated by an activity sensor of physical preponderance such as an accelerometer), then the device delivers a cardiac stimulation at a frequency that is slightly higher than the natural sinusal rate/rhythm of the patient. This increased frequency is provided to increase the blood flow in order to be able to reduce the incidence of the oxygen desaturation caused by a SAS.

The starting point of this invention lies in the observation by the inventors that a systematic increase of the heart rate in response to a detection of apnea or hypopnea is not always a suitable treatment. Indeed, it has been reported that for certain patients the apnea or hypopnea could be followed by an adrenergic reaction. Such a reaction naturally induces a light tachycardia and a significant increase in blood pressure, sufficient to compensate for the fall of the ventilatory activity. Among these patients, the myocardium thus can react naturally by adapting its contractility so as to increase the blood flow. In this way, the myocardium maintains the blood appreciably at the same level of oxygen saturation.

Ideally, to decide whether or not it is necessary to apply to the myocardium a stimulation at a frequency higher than the natural sinusal rate/rhythm of the patient, the best criterion would be a direct measurement of oxygen saturation in blood. Then, the stimulation would be started only in the event of a proven and significant desaturation. But such a direct measurement of oxygen saturation is difficult to implement in a simple and permanent manner in the context of an active implanted medical device, given the current state of the art.

OBJECTS AND SUMMARY OF THE INVENTION

Broadly, the present invention proposes to overcome the aforementioned deficiency in the treatment of the apnea and the hypopnea by estimating variation of contractility of the myocardium by use of an hemodynamic sensor. Thus, in the event of a detected anomaly in the respiratory activity (i.e., an apnea or hypopnea), before taking any therapeutic action, the device estimates whether or not there was a correlative modification of the myocardium contractility:

1. If the hemodynamic sensor indicates the occurrence of a notable hemodynamic fall, revealing that the myocardium could not naturally adapt its contractility following the anomaly, or did not adapt sufficiently, then the device takes an action in order to compensate for the oxygen desaturation induced by the respiratory disorder. For example, if the hemodynamic fall and associated inadequate myocardium contractility follows an apnea or an hypopnea, then a stimulation is triggered at a frequency that is higher than the natural sinusal rate/rhythm.

2. In the contrary case, i.e., if the hemodynamic sensor delivers a signal indicative of stable or not very evolutionary hemodynamic information, the device does not take an action, because this situation probably reveals that there no was desaturation requiring a recovery by an increase of the blood flow.

In other words, the invention proposes, in the event of a detected respiratory anomaly, to adapt the reaction of the device according to the stabilization of the hemodynamic information, which provides an estimate of the variations of contractility, correlated to the increases in blood pressure. It is noted that the analysis of hemodynamic information can be based on hemodynamic information collected (sensed) before or after the respiratory anomaly.

One aspect of the present invention is therefore directed to a device of the type that is described by the above mentioned EP A 0 970 713 and corresponding U.S. Pat. No. 6,574,507 B1, i.e., an implantable medical device that includes circuit structure and functionality able to measure the respiratory activity and deliver a signal representative of ventilatory activity of the patient, and circuit means for analyzing the ventilatory activity signal to detect the occurrence of a respiratory apnea, a respiratory hypopnea or both.

In accordance with the present invention, the device also includes a hemodynamic sensor that is able to deliver a hemodynamic signal that is representative of the contractility of the myocardium, and circuit means for analyzing the delivered hemodynamic signal and detecting an occurrence of a variation of the myocardium contractility, and means for conditionally modifying an operating parameter of the device in the event of a detected hemodynamic state variation in relation to the detection of an apnea or of a hypopnea (either before or following the detection). In other words, the detection of the variation of the detected hemodynamic state can be performed equally as well after as before the detection of the apnea or the hypopnea. In this regard, the device requires a period of time to declare, e.g., an apnea, such as 10 seconds. During this time, the hemodynamic signal has significantly decreased. Thus, it is possible to respond to the decrease and begin accelerating the pacing to compensate for the fall before the "official" detection of an apnea.

Preferably, hemodynamic sensor includes circuits for measuring an intracardiac impedance, or a sensor for measuring an endocardial acceleration.

Preferably, the conditionally modification means operates to modify in a temporary manner an operating parameter of the device, and then restore this same operating parameter to its previously set value when the analysis of the delivered hemodynamic signal no longer detects any variation of the hemodynamic state. The operating parameter of the device that is conditionally modified can be selected from among the following:

1. The stimulation frequency, where the frequency is increased in the event of a determined variation of the detected hemodynamic state in relation to the detection of an apnea or a hypopnea.

2. The atrio-ventricular delay, wherein the delay is shortened in the event of a determined variation of the detected hemodynamic state in relation to the detection of an apnea or a hypopnea, or 3. For a device including multisite stimulation functionality, the stimulation mode, wherein the means of conditionally modifying means operates to trigger a multisite stimulation in the event of a detected hemodynamic state variation in relation to the detection of an apnea or of a hypopnea. A multisite stimulation mode is known to persons of ordinary skill in the art, as described, for example, in U.S. Pat. No. 6,253,106 B1, which is commonly assigned herewith and the disclosure of which is incorporated herein by reference. A multisite cardiac stimulation device typically includes at least a right and a left ventricular electrode for stimulating the right and left ventricle, as well as a right atrial electrode for delivering an atrial stimulation (and optionally a left atrial electrode for stimulating the left atrium), such that each chamber can be independently stimulated under appropriate control logic implementing known therapies for multisite pacing.

In a preferred embodiment, the hemodynamic signal analyzing means functions to compare the hemodynamic signal measured at the cardiac cycle following the respiratory cycle during which the apnea or hypopnea occurred, with an average of the hemodynamic signals acquired prior to the respiratory cycle during which the apnea or hypopnea occurred.

In another preferred embodiment, the hemodynamic signal analyzing means functions to compare the hemodynamic signal measured after a plurality of cardiac cycles following the respiratory cycle during which the apnea or hypopnea occurred, with an average of the hemodynamic signals acquired prior to the respiratory cycle during which the apnea or hypopnea occurred.

BRIEF DESCRIPTION OF THE DRAWINGS

Further benefits, features and characteristics of the present invention will become apparent to a person of ordinary skill in the art in view of the following detailed description of preferred embodiments of the invention, made with in reference to the annexed drawings, in which:

FIG. 1 is a flowchart of a first embodiment of the invention; and

FIG. 2 is a flow chart of a second embodiment of the invention.

DETAILED DESCRIPTION OF THE INVENTION

The device in accordance with the present invention comprises means for detecting an occurrence of apnea or of hypopnea by an analysis of the respiration rate of the patient during his sleep, this rate/rhythm being given by the evolution over the course of the time of the minute ventilation signal (signal MV).

Signal MV is a parameter with physiological preponderance (i.e., predominantly physiological in nature) that is obtained by a measurement of intrathoracic (or intracardiac) impedance. This measurement, in itself well known, is commonly operated between two electrodes laid out in the patient's rib cage, or between an electrode (for example, a stimulation electrode, if the implanted device is a cardiac pacemaker) and the case of the implanted device. The impedance is measured as a voltage in response to an injection of a constant current pulse of a few hundred microamperes, at a frequency of a few Hertz, typically 8 Hz. This technique, for example, is described by Bonnet J L et al., "Measurement of Minute-Ventilation with Different DDDR Pacemaker Electrode Configurations," PACE, Vol. 21, 98, Part 1, and it is implemented in the Chorus RM 7034 brand pacemaker devices, commercially available from ELA Médical.

In addition, the device comprises means for detecting the phases of sleep of the patient, in order to proceed to the study of the apnea or hypopnea only during the detected sleep phases. This constraint is used because the variations of respiratory activity occurring during a phase of awakening are not normally pathological.

Although the precise manner of detecting a sleep phase is not important to the invention, one suitable technique is to diagnose sleep by using a physiological sensor for measuring the minute ventilation, possibly in combination with a sensor for measuring activity, a parameter having a physical preponderance such as acceleration, as described in the EP-A 0 750 920 and its corresponding U.S. Pat. No. 5,722,996 and EP A-0 770 407 and its corresponding U.S. Pat. No. 5,766,228, each commonly assigned herein to ELA Medical, which U.S. Pat. Nos. 5,722,996 and 5,766,228 are incorporated herein by reference in their entirety.

The device considers that there is apnea when it detects a cessation of respiratory activity of a duration longer than 10 seconds. This is a phenomenon that is simple to detect by monitoring signal MV. To detect hypopnea, the device can, for example, compare different sliding averages of signals MV, which averages are established, for example, over 10 seconds duration. If between two such consecutive averages a significant decrease of the ventilation minute is detected, for example, a decrease of more than 50%, then the device considers that there is hypopnea.

Furthermore, to allow the implementation of the invention, the device comprises an hemodynamic sensor making it possible to estimate the variations of myocardium contractility, which are correlated with the increases in blood pressure. This hemodynamic state parameter is more sensitive and varies more rapidly than the measure of the heart rate variations, to estimate better the consequences of the oxygen desaturation.

The hemodynamic sensor can be in particular an endocardial acceleration sensor of the type PEA (Peak Endocardial Acceleration) as described, for example, in the EP-A 0 515 319 and its corresponding U.S. Pat. No. 5,304,208, EP-A 0 582 162 and its corresponding U.S. Pat. No. 5,454,838, or EP-A 0 655 260 and its corresponding U.S. Pat. No. 5,496,351 (which are assigned to Sorin Biomedica Cardio SpA), and which U.S. patents are incorporated herein by reference in their entirety. A suitable commercial device for measuring heart acceleration is available from Sorin Biomedica Cardio SpA under the trade name Living CHF, and an electrode having an accelerometer at its tip also is available from Sorin under the trade name Best. The hemodynamic sensor can be also a sensor of endocardiac impedance, for example, a sensor of transvalvular bio-impedance, as described by the EP-A 1 116 497 and its corresponding U.S. Pat. No. 6,604,002, or of trans-septum bio-impedance, as described by the EP-A 1 138 346 and its corresponding published U.S. Patent Application US2001/0034540 A1 011029, both in the name of ELA Medical which U.S. patent and publication are incorporated herein by reference in their entirety.

One now will describe more particularly, with reference to the flow chart of FIG. 1, a first embodiment by which the invention can be implemented. The device, after having awaited the end of a respiratory cycle (stage 10), determines whether an apnea or an hypopnea has occurred (stage 12), i.e., if it found a cessation of the respiratory cycle of a duration longer than 10 seconds or a fall of the respiratory flow by more than 50%. In the negative case, no action is taken and the device continues to monitor (analyze) the respiration rate (stage 10). In the affirmative case, on the other hand, the device analyzes whether or not there were a significant variation of the hemodynamic state consecutive to the detected apnea or this hypopnea (stage 12).

To this end, after having awaited the end of the currently running cardiac cycle (stage 14), the device determines (stage 16) whether the hemodynamic sensor detected a fall of the hemodynamic signal greater than a given reference threshold. This reference threshold is preferably a dynamic threshold made up, for example, by an average, over a plurality of cardiac cycles, of the signal values delivered by the hemodynamic sensor. The average considered is in this embodiment preferably based on values of signals acquired prior to the respiratory cycle presenting the anomaly, i.e., prior to the respiratory cycle detected at the end at stage 10.

In the event of a demonstrable hemodynamic fall, which one would expect results in a reduction in the oxygen saturation in blood because of the apnea or of the hypopnea, then the device increases the frequency of stimulation by a step (stage 18). This small increase in frequency (a step of increase being typically selected from between 1 and 5 bpm) makes it possible to compensate for the oxygen desaturation. In alternative embodiments, or to complement the heart rate, other operating parameters of the pacemaker can be modified: one can thus consider, for example, shortening the AV delay and/or the triggering of a multisite stimulation.

The algorithm is then repeated in the same way as previously. The increase in the stimulation frequency at stage 18 normally results in an improvement of the hemodynamic state of the patient. If this improvement is not sufficient to lead to a stabilization of hemodynamic information, the device will still detect a hemodynamic fall (at stage 16 of the following iteration) and will increase by an additional step the stimulation frequency (at the subsequent stage 18).

On the other hand, if the increase in the stimulation frequency, by one or more steps (i.e., after one or more iterations), led to an hemodynamic stabilization of the state, an absence of significant variation of the signal, detected at stage 16, will lead to a test at stage 20 where the device compares the current stimulation frequency $F_{STIM}$ to a reference frequency $F_{PROG}$, e.g., a preprogrammed frequency.

If the stimulation frequency $F_{STIM}$ is higher than pre-programmed frequency $F_{PROG}$, then the device decreases the stimulation frequency by one step (stage 22) before returning to the starting point (stage 6) of the flow chart. Thus, by successive step adjustments, in increased or decreased directions, the stimulation frequency $F_{STIM}$ could be continuously adjusted to the effective minimum. This in turn makes it possible to obtain a more precise stabilization of the hemodynamic state, without exceeding this value by more than one step.

FIG. 2 illustrates a second embodiment of the present invention, in which the same reference numbers are used for the stages that are the same as the stages described in connection with FIG. 1. In this alternative embodiment, the device operates the test of stage 16 (same as in FIG. 1) on the hemodynamic signal, but not on the cardiac cycle which immediately follows the detected apnea or hypopnea at stage 12, and rather only after N cardiac cycles following the detected apnea or hypopnea.

For this purpose, the algorithm counts the number of past cycles (stage 24, counter N) and compares the value of counter N with a programmed value prog (stage 26), for example, N=5 cycles (prog=5). Thus, at the start (stage 8), the count value N is reset to equal to zero. This embodiment is believed to make it possible for an adrenergic reaction, suitable to induce a significant modification of the hemodynamic state, to express itself naturally without need for taking a therapeutic action.

It should be understood that the test for the sleep state (stage 8), illustrated in FIGS. 1 and 2 as outside of the monitoring of the respiratory cycle, equally may be located within the monitoring of the respiratory cycle, as a matter of design choice. Preferably, the patient is known to be in a sleep phase when the present invention is being used.

Suitable devices for which the present invention has application include, for example, the active implantable medical devices available from Ela Médical, Montrouge France. These devices are microprocessor-based systems having circuits for receiving, conditioning and processing detected electrical signals, and that are capable of receiving software instructions by telemetry, storing them in memory, and then executing those instructions to perform the functions described above in implementing the present invention. The creation of suitable software instructions for controlling an implant to perform the aforementioned functions of the present invention are believed to be within the abilities of a person of ordinary skill in the art. The detection circuits used to detect the cardiac signals in the atrium and the ventricle, in the left and/or right chambers, are well known and any suitable design may be used. The circuits used to inject the currents to obtain the bioimpedance measurements are known as well from, for example, EP 1 116 497 and corresponding U.S. Pat. No. 6,604,002 B1 and EP 1 138 346 and corresponding U.S. Published Pat. Application 2001-0034540, and any suitable circuit to may be used. The activity sensor used and the determination of rest phases might be taken from the devices disclosed in, for example, U.S. Pat. No. 5,722,996 and EP1317943 and its corresponding U.S. Published Patent Application 2003-0163059, which disclosures are incorporated herein by reference.

One skilled in the art will appreciate that the present invention can be practiced by other than the described embodiments, which are presented for purposes of illustration and not of limitation.

We claim:

1. An active implantable medical device comprising:
   means for measuring respiratory activity having an output signal representative of ventilatory activity of the patient;
   means for analyzing the ventilatory activity signal and detecting an occurrence of a respiratory apnea and an occurrence of a respiratory hypopnea;
   means for measuring a hemodynamic state having an output hemodynamic signal representative of the contractility of the myocardium, means for analyzing the hemodynamic signal and detecting an occurrence of a variation of the contractility;
   means for determining whether the detected contractility variation is significant; and
   means for conditionally modifying an operating parameter of the device to treat a detected apnea or hypopnea when said detected contractility variation is significant.

2. The device of claim 1, wherein means for determining whether the contractility variation is significant further comprises means for operating said analyzing means to analyze said hemodynamic signal detected after detection of said apnea or hypopnea.

3. The device of claim 2, wherein the hemodynamic signal analyzing means further comprises means for comparing a first hemodynamic signal measured during a cardiac cycle following the respiratory cycle during which the apnea or hypopnea was detected, with an average of the hemodynamic signals acquired prior to said respiratory cycle.

4. The device of claim 2, wherein the hemodynamic signal analyzing means further comprises means for comparing a first hemodynamic signal measured after a plurality of cardiac cycles following the respiratory cycle during which the apnea or hypopnea was detected with an average of the hemodynamic signals acquired prior to said respiratory cycle during which the apnea or hypopnea was detected.

5. The device of claim 1, wherein the means for determining whether the contractility variation is significant further comprises means for operating said analyzing means to analyze said hemodynamic signal detected before detection of said apnea or hypopnea.

6. The device of claim 1, wherein the hemodynamic measuring means further comprises means for measuring an intracardiac impedance.

7. The device of claim 1, wherein the hemodynamic measuring means further comprises means for measuring an endocardial acceleration.

8. The device of claim 1, wherein said operating parameter has a first value and said conditionally modifying means further comprises means for modifying in a temporary manner said operating parameter to a second value different from said first value.

9. The device of claim 8, wherein said conditionally modifying means further comprises means for restoring said operating parameter to said first value in response to said hemodynamic signal analysis means no longer detecting a variation of myocardium contractility.

10. The device of claim 1, wherein said operating parameter is a stimulation frequency, and said conditional modification is an increase in response to a detected significant variation and a detected apnea or hypopnea.

11. The device of claim 1, wherein said operating parameter is an atrio-ventricular delay and said conditional modification is a shortened delay in relation to a detected significant variation and a detected apnea or hypopnea.

12. The device of claim 1, wherein said device further comprises means for stimulating a patient's heart having at least a first stimulation mode for delivering a multisite stimulation, wherein said operating parameter is a mode of cardiac stimulation, and said conditional modification comprises means for operating said stimulation means to trigger a multisite stimulation in relation to said detected significant variation and a detected apnea or hypopnea.

13. The device of claim 1, wherein said device further comprises means for comparing a detected contractility variation to a reference threshold, and determining a significant variation in response to said contractility variation being greater than said threshold.

* * * * *